(12) United States Patent
Matusch (10) Patent No.: US 8,663,193 B2
(45) Date of Patent: Mar. 4, 2014

(54) DISPOSABLE INJECTOR WITH A MANUALLY ACTUATED PISTON AND WITH A TWIN CHAMBER SYSTEM

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 13/534,133

(22) Filed: Jun. 27, 2012

(65) Prior Publication Data

US 2012/0271279 A1    Oct. 25, 2012

Related U.S. Application Data

(60) Division of application No. 12/800,835, filed on May 24, 2010, now Pat. No. 8,257,309, which is a continuation-in-part of application No. PCT/EP2008/010251, filed on Dec. 4, 2008.

(30) Foreign Application Priority Data

Jan. 1, 2008 (DE) .......................... 10 2008 003 105

(51) Int. Cl.
*A61M 31/00* (2006.01)
*A61M 1/00* (2006.01)

(52) U.S. Cl.
USPC .......................................... 604/518; 604/152

(58) Field of Classification Search
USPC ............................................................ 604/518
See application file for complete search history.

(56) References Cited

U.S. PATENT DOCUMENTS 5,060,704 A    10/1991 Rohrbough
2001/0021820 A1 *  9/2001 Lynn .............................. 604/90

FOREIGN PATENT DOCUMENTS

WO    WO 00/23133    4/2000
WO    WO 03/090822 A1    11/2003

OTHER PUBLICATIONS

Written Opinion of the International Searching Authority for the corresponding international application—PCT/EP2008/010251.

* cited by examiner

*Primary Examiner* — Jason Flick
(74) *Attorney, Agent, or Firm* — R. S. Lombard; K. Bach (57) ABSTRACT

A method for preparing a solution from a solvent and an active substance in and on a disposable injector with a housing, with an at least intermittently fillable cylinder/piston unit which is arranged thereon and has a manually movable piston, and with a detachable container adapter mounted upstream of the cylinder/piston unit, wherein the container adapter supports a container which can be filled at least temporarily with active substance and which is closable by an openable stopper.

2 Claims, 7 Drawing Sheets

DISPOSABLE INJECTOR WITH A MANUALLY ACTUATED PISTON AND WITH A TWIN CHAMBER SYSTEM

CROSS-REFERENCE TO RELATED APPLICATION

This application is a divisional of and claims the benefit of U.S. patent application Ser. No. 12/800,835 filed May 24, 2010, now U.S. Pat. No. 8,257,309 which is incorporated herein by reference in its entirety. The said U.S. patent application Ser. No. 12/800,835 is a continuation-in-part application of pending international application PCT/EP2008/010251 filed Dec. 4, 2008 and claiming the priority of German Application No. 10 2008 003 105.4 filed Jan. 1, 2008.

BACKGROUND OF THE INVENTION

The invention relates to a method for preparing a solution from a solvent and an active substance in and on a disposable injector with a housing, with an at least intermittently fillable cylinder/piston unit which is arranged thereon and has a manually movable piston, and with a detachable container adapter mounted upstream of this cylinder/ piston unit, wherein the container adapter supports a container which can be filled at least intermittently with active substance and which is closed by an openable stopper.

WO 00/23133 discloses, among other things, an injector of this kind. Between the container partially filled with lyophilisate and the cylinder/piston unit, which here is a cartridge closed at the front by means of a lid and at the rear by means of a piston, a needle carrier with a twin-end injection needle sits in the container adapter. By pushing the container forwards into the container adapter, the front end of the needle pierces the seal of the container. By screwing the container adapter into the injector, the rear end of the needle pierces the lid of the cartridge. The needle carrier is at the same time permanently adapted to the cartridge. The liquid in the cartridge is pumped into the container, where the lyophilisate dissolves. The solution is then pumped back into the cartridge. After removal of the container adapter, the spring of the injector is tensioned manually in order to make this ready for injection.

The object of the present invention is to develop a method for making a solution using a modular disposable injector which stores a liquid and an active substance in each case separately and in a sterile manner and which provides a space in which the active substance, for its application, is dissolved in the liquid or mixed with the liquid.

SUMMARY OF THE INVENTION

The invention relates to a method for making a solution from a solvent and an active substance in and on a disposable injector with a housing, with a cylinder/piston unit which is arranged thereon and has a manually movable piston, and with a detachable container adapter mounted upstream of this cylinder/piston unit, wherein the container adapter supports a container that is closed by an openable stopper. The piston of the cylinder/piston unit is movable via a pump rod. The container adapter engages at the front end around the cylinder of the piston/cylinder unit. The container adapter has an intermediate floor which supports a dual adapter having at least one through-channel. The container, which bears tightly with its stopper on the dual adapter, sits longitudinally displaceably in the rear of the container adapter. The container is opened by displacing it towards the intermediate floor and pushing the stopper into the container. With the present invention, a method is developed for making a solution form a solvent and an active substance in a disposable injector which stores a liquid and an active substance in each case separately and in a sterile manner and provides a space in which the active substance, for its application, is dissolved in the liquid or mixed with the liquid.

The piston of the cylinder/piston unit is used to practice the method of the present invention and is movable separately via a pump rod. The container adapter engages at the front at least partially around the cylinder of the cylinder/piston unit. The container adapter has an intermediate floor which bears at least partially on the free end face of the cylinder and which has a recess for a dual adapter having at least one through-channel. The container sits longitudinally displaceably in the rear of the container adapter and, in the delivery state, bears tightly with its stopper on the dual adapter and is held and secured at the rear by a cap. The container is opened by displacing it towards the intermediate floor and pushing the stopper into the container.

The present invention provides a method for preparing a solution from a solvent and an active substance in and on a disposable injector. Before the solution is prepared, the solvent is stored in an injector-side cylinder/piston unit, while the active substance is contained in a container which is mounted upstream of the cylinder/piston unit and which is closed by a stopper. A dual adapter with a bore extending through it is arranged between the cylinder/piston unit and the stopper. To establish a connection between the interior of the cylinder of the injector-side cylinder/piston unit and the interior of the container, the container is displaced towards the dual adapter, forcing the stopper out. The solvent flows into the interior of the container when the piston is pushed in. There, the active substance dissolves in the solvent to form a solution. The solution is pumped into the cylinder/ piston unit by the injector-side piston being pulled back. The solution can be a suspension or an emulsion.

The method of the present invention utilizes, for example, a needleless disposable injector whose cylinder/piston unit can be emptied or filled by a manual pump movement of its piston when a spring-energy reservoir is tensioned. For this purpose, for example, a pump rod is coupled from outside into the piston of the cylinder/piston unit arranged in the injector, such that the piston can be moved by means of the pump rod. If appropriate, the pump rod is uncoupled and withdrawn from the housing before the injector is used.

To practice the method of the present invention a container is mounted upstream of the cylinder/piston unit and is guided displaceably in a container adapter secured on the injector. A solvent, e.g. water for infusion purposes, is stored in a sterile manner in the cylinder/piston unit. The upstream container holds a freeze-dried medicament, similarly packaged in a sterile manner. Immediately prior to the use of the disposable injector, the water is conveyed into the container to the medicament, where a solution, a suspension or an emulsion forms. This liquid is pumped back into the injector-side cylinder/piston unit in order then to be able to be injected. No lumps get into the cylinder space of the first cylinder/piston unit during the transfer-pumping, as a result of which a precise injection stream is guaranteed.

The container is mounted hydraulically upstream of the injector-side cylinder/piston unit. According to the illustrative embodiment, it sits spatially in front of the cylinder/piston unit. However, the container can also be arranged on the side of the injector. In this case, it would sit parallel alongside the cylinder/ piston unit.

BRIEF DESCRIPTION OF THE DRAWINGS

Further details of the invention are set forth in the following schematic illustrative embodiments.

FIG. 17 shows the same as FIG. 15, but with the container pushed in;

DETAILED DESCRIPTION OF THE PARTICULAR EMBODIMENTS

FIGS. 1 to 5 show simplified schematic diagrams of a disposable injector type, with a permanently charged spring-energy reservoir, with a filled cylinder of the cylinder/piston unit, and with an attached active substance container, in different states of pumping and triggering. The disposable injector shown comprises a housing (10), a cylinder/piston unit (100) pre-filled with an injection solution for example, a piston-actuating ram (60), and a helical compression spring (50) as spring-energy reservoir. A trigger element (82) and a safety element (90) are also arranged on the housing (10). The cylinder/piston unit (100) is sealed at the front by a container adapter (200) in combination with a dual adapter (240). The cylinder/piston unit (100) has a piston (111), which can be moved in the cylinder (101) by means of a separate pump rod (140).

Figure 1:
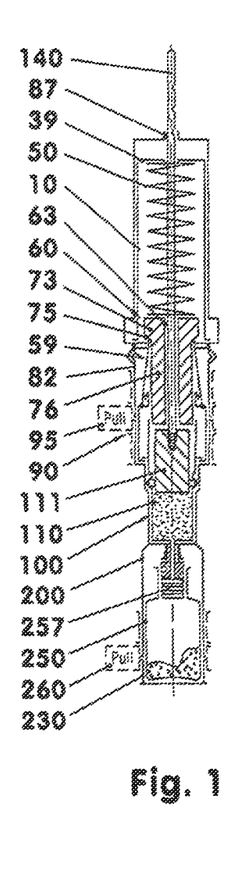
FIG. 1 shows a disposable injector with a solvent-filled cylinder/piston unit, and with an attached container partially filled with active substance.
Figure 2:
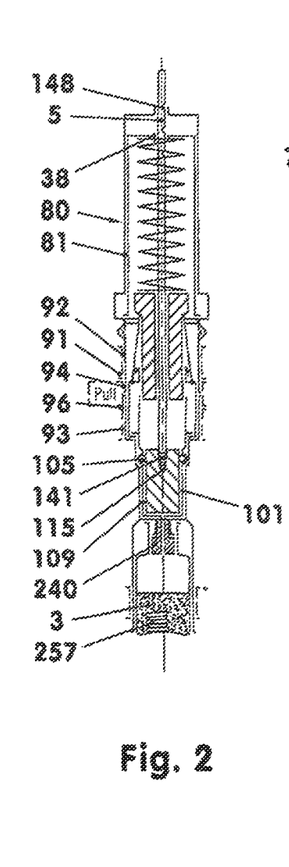
FIG. 2 shows the same as FIG. 1, but with the solvent pumped into the container partially filled with active substance.
Figure 3:
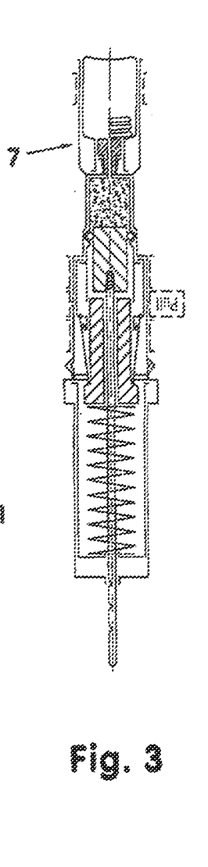
FIG. 3 shows the same as FIG. 1, but with the solution sucked back from the container into the cylinder of the cylinder/piston unit.
Figure 4:
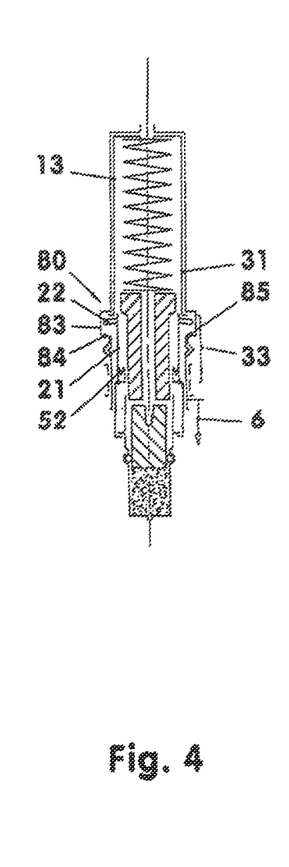
FIG. 4 shows the disposable injector after removal of the container, priming and actuation, a hypothetical state.
Figure 5:
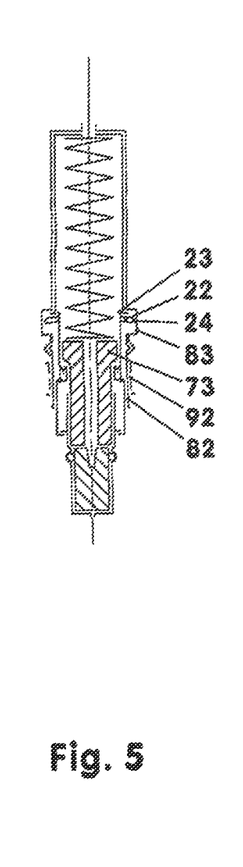
FIG. 5 shows the same as FIG. 4, but after the solution has been expelled.

A container (250) sits longitudinally displaceable in the container adapter (200).

The housing (10) is a pot-shaped hollow body, open at the bottom and with a floor (39) at the top. In the middle area, the jacket area (31), cf. FIG. 4, the housing (10) has, for example, two window-like apertures (33) lying opposite each other. A pressure bar (21) is mounted in an articulated manner on the lower edge of each individual aperture (33). The floor (39) has a central bore (38).

The pressure bars (21) are arranged here, only by way of example, in pivot hinges and are supported on the housing (10) via spring elements (52). The spring elements (52) press the support bars (21) at least approximately radially outwards against the trigger element (82), cf. FIGS. 1 to 5. There, they rest on the trigger element (82) via cams (22). The cams (22) can, for example, also lie 5 to 20 millimetres below the respective free upper end of the pressure bars (21). If the pressure bars (21) are formed integrally on the housing (10), cf. FIG. 6 among others, they spring outwards as elastic flexural beams (28).

The two pressure bars (21), subjected to pressure, hold the piston-actuating ram (60) in its pretensioned position at the ram plate (73) thereof, cf. FIG. 1. For this purpose, the pressure bars (21) rest with their support surfaces (23) on the ram plate (73). The size of the respective contact surface between a support surface (23) and the corresponding site on the ram plate (73) is in the range of 2 to 20 mm$^2$.

On the side directed away from the centre line (5), each pressure bar (21) has a contact surface (24) on its cam (22).

In the lower area of the housing (10) there are holding elements for securing the cylinder-piston unit (100).

In the illustrative embodiment, the cylinder/piston unit (100) comprises a transparent cylinder (101) which is filled with a solvent (1), e.g. water for infusion purposes, and in which a piston (111) sits in the rear position. The cylinder (101) has a cylinder inner wall (109) which, towards the rear, ends in an annular groove, for example. A sealing element (105), bearing tightly on the piston (111) in a radial direction, sits in the annular groove. The filled cylinder interior (110) is closed off in a sterile manner by the piston (111) and the sealing element (105). Behind the annular groove, the cylinder (101) widens to such an extent that a rearwardly moved piston (111) cannot touch the wall of the widened area.

On its rear face, the piston (111) has a for example central, frustoconical recess (115) into which the pump rod (140) is screwed by means of a tapered thread (141). The pump rod (140) can be released from the piston (111) with minimal force.

Above the piston (111), the piston-actuating ram (60) is arranged in the housing (10) in such a way, for example, that although not touching the piston, it is guided laterally with its lower end, for example, in the upper area of the cylinder (101). The piston-actuating ram (60) has a for example central bore (63) through which the pump rod (140) extends with considerable play.

According to FIG. 1, the lower half of the housing (10) is enclosed by the sleeve-like trigger element (82). The trigger element (82) is mounted longitudinally displaceably on the radial outer surface (13) of the housing (10). It ends at the rear with a sharp edge (85). Below the edge (85), cf. FIG. 5, the outer contact surfaces (24) of the cams (22) according to FIGS. 1 to 3 touch the inner wall (59) of the trigger element (82) in a securing manner.

A trigger cap (81) is secured on the trigger element (82), for example near the edge (85), and completely surrounds the rear end of the housing (10). It has a central bore (87) there for passage of the pump rod (140). The trigger cap (81) comprises a peripheral widened area (83) in which the cams (22) are received when the injector is triggered. In the case of a nonrotationally symmetrical trigger element (82), this widened area (83) can also be replaced by partial widened areas per pressure bar (21) or uncovered openings.

With respect to the housing (10), the widened area (83) is positioned and dimensioned so precisely that it can receive the cams (22) of the outwardly forced pressure bars (21) as they retreat during the triggering procedure. The inner contour of the widened area (83) is, for example, a channel with a return flank (84), which here represents a plane perpendicular to the centre line (5) of the injector.

The piston-actuating ram (60) arranged in the housing (10) is divided into two areas. The lower area is the piston slide (76). Its diameter is somewhat smaller than the internal diameter of the rear area of the cylinder (101). The lower end face of the piston slide (76) acts directly on the piston (111).

The upper area of the piston-actuating ram (60), that is to say the ram plate (73), is a flat disc which is cylindrical at least in some areas and whose external diameter is a few tenths of a millimetre smaller than the internal diameter of the housing (10) in the jacket area (31). The lower end face has a collar surface (75) arranged around the piston slide (76). It has the shape of a frustoconical jacket whose apex angle is ca. 100 to 130, preferably 120 degrees. The notional tip of the frustoconical jacket lies on the centre line (5) in the area of the piston slide (76). The collar surface (75) can also be spherically curved.

The piston slide (76) can of course also be designed as a separate component from the ram plate (73). For this purpose, it is then guided on the inner wall of the housing (10).

The helical compression spring (50) sits pretensioned between the ram plate (73) and the upper floor (39) of the housing (10). The spring force of the helical compression spring (50) is transmitted to the pressure bars (21) via the ram plate (73). Because of the inclination of the collar surface (75), the pressure bars (21) are forced radially outwards in the manner of a spline gear. The trigger sleeve (82) permanently supports this radial force.

Located below the trigger element (82) is the container adapter (200), which is closed with a stopper (257) and in which the container (250), partially filled with a lyophilisate for example, is arranged. The container (250) is secured on the container adapter (200) via a cap (230) and a tear-off banderole (260). A dual adapter (240) with a bore extending through it sits between the container (250) and the cylinder (101).

After removal of the tear-off banderole (260) and of the cap (230), the container (250) is displaced towards the dual adapter (240) in order to force the stopper (257) into the container (250). The piston (111) can now be pushed into the cylinder (101) by means of the manually actuated pump rod (140) in order to force the solvent (1) into the container (250). The solution (3) forms in the latter. According to FIG. 3, this solution is pumped back into the cylinder (101) by pulling on the pump rod (140).

To complete the suctioning operation, the gas bubbles that may have been sucked into the cylinder (101) are removed in a known manner, for example by pushing the piston (111) slightly back. Then, for example, the smooth pump rod (140) is unscrewed from the recess (115) of the piston (111) and withdrawn from the housing (10).

To prime the injector, the tear-off banderole (94) is pulled off such that the adhesive connection between the container adapter (250) and the trigger element (82) is broken. The container adapted (250) is pulled off. The disposable injector is positioned on the injection site. The trigger element (82) can now be displaced in the direction of the cylinder/piston unit (100), cf. FIG. 4. In this procedure, the trigger element (82) slides linearly down the outer wall (13) of the housing (10), that is to say in the direction of the injection site. The contact surfaces (24) of the pressure bars (21) slip over the edge (85) and spring radially outwards into the widened area (83) under the force of the spring element (50). The piston-actuating ram (60) shoots downwards without any obstruction, cf. FIG. 5. The cylinder (100) is emptied.

Instead of a linear sliding movement of the trigger element (82) on the housing (10), a helical movement can also be provided. In this case, the trigger element (82) and the housing (10) are guided on each other, e.g. via a sliding block and a slot. If appropriate, the triggering can also be achieved by a pure pivoting movement between the housing (10) and the trigger element (82). The pivot axis would in this case be the centre line (5).

FIGS. 6 to 11 show an embodiment of the principle described in FIGS. 1 to 5. Here, the load-bearing component is a one-piece housing (10). It is made from, for example, a fibreglass-reinforced polyamide by injection moulding. The housing (10) has a substantially tubular shape and is divided up into two functional areas, that is to say, on the one hand, the upper jacket area (31) and, on the other hand, the lower fixing area (41).

Figure 10:
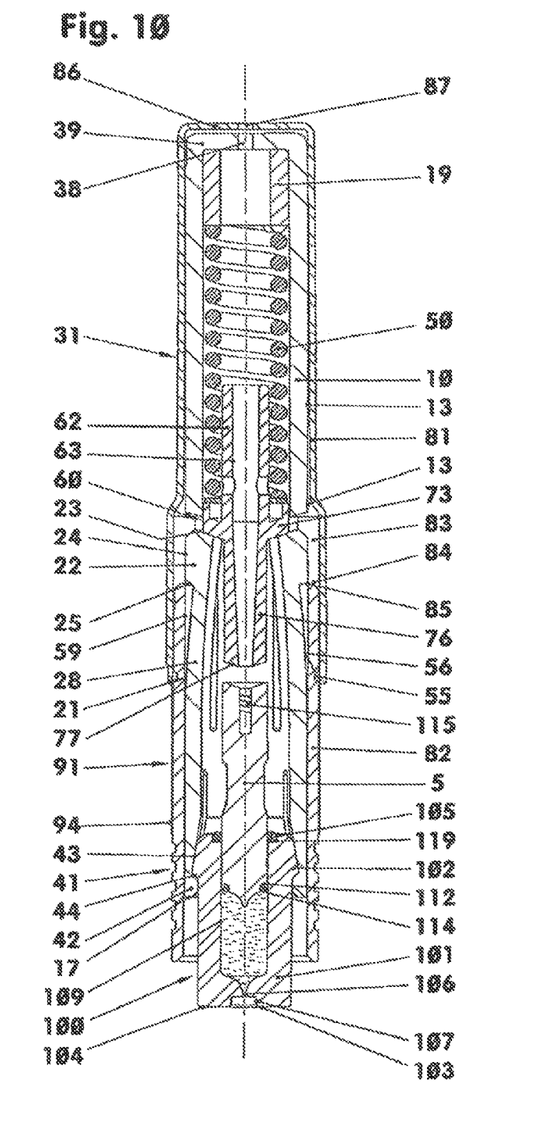
FIG. 10 shows the disposable injector after removal of the container adapter, priming and actuation, a hypothetical state.

The substantially tubular jacket area (31) is sealed at the top by a for example planar floor (39) with an integrated bore (38), cf. FIG. 10. Located in the lower half of the jacket area (31), there are two integrally formed pressure bars (21) lying opposite each other. The pressure bars (21) are integrally formed thereon at a location just above the fixing area (41). For formation of the respective pressure bar (21), a narrow, at least approximately U-shaped gap is located in the lower area of the jacket section (31) and surrounds the individual pressure bar to the sides and at the top. Along ca. 80% of its length, the pressure bar (21) has the wall thickness and curvature of the wall of the housing (10). This area also has, among other things, the function of a resiliently elastic flexural beam (28). It has a crescent-shaped cross section.

Figure 8:
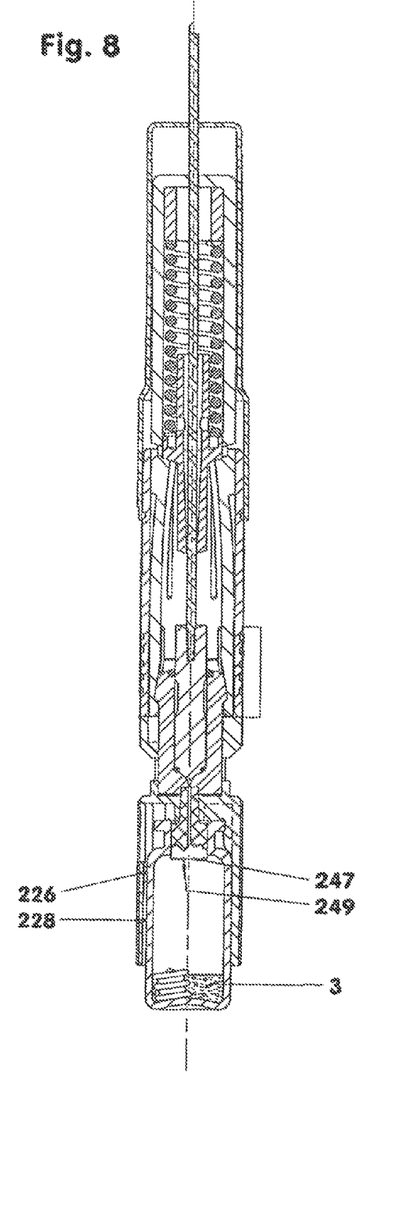
FIG. 8 shows the same as FIG. 7, but with the cylinder emptied and the container filled.

If appropriate, a part of this flexural beam (28) can also be provided with a rectangular cross section in order to reduce bending stresses that arise during use in the edge area of the flexural beam. In FIG. 8, the pressure bar (21) is shown in the undeformed state.

The upper free end here of the individual pressure bar (21) is formed by the radially outwardly projecting cam (22). The latter has at least one support surface (23) and one contact surface (24). According to FIG. 10, the ram plate (73) of the tensioned disposable injector lies with its collar surface (75) on the support surface (23). The support surface (23), which here fulfills the function of a wedge surface, has the form of a frustoconical jacket with an apex angle of 120 degrees.

If appropriate, the pressure bars (21) or the collar surface (75) have a ceramic armouring, at least in the contact area. If appropriate, the collar surface (75) is reinforced by, for example, an affixed washer of frustoconical shape.

Figure 11:
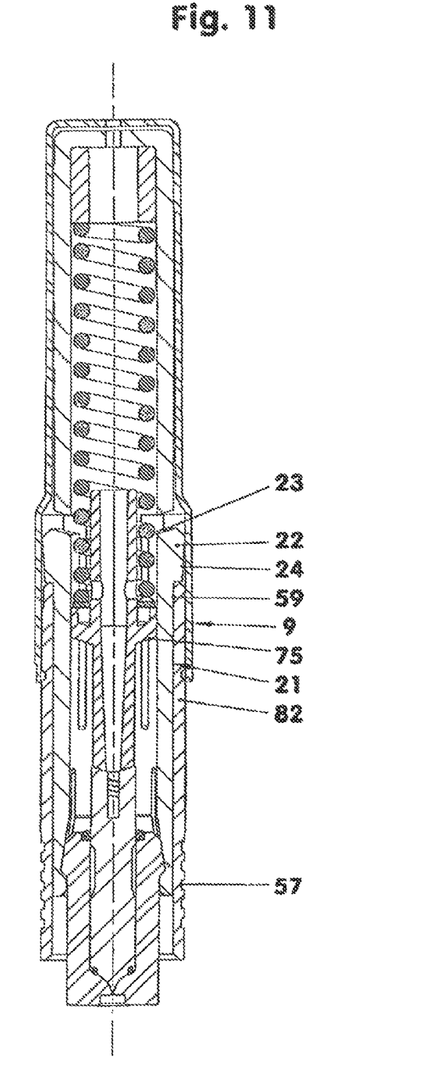
FIG. 11 shows the same as FIG. 10, but after the solution has been expelled.

The contact surface (24) of the cams (22), cf. FIG. 11, is part of a cone whose maximum diameter is, for example, 3 to 4 millimetres greater than the external diameter of the housing (10). When the disposable injector is tensioned, the contact surface (24) touches the inner wall (59) of the sleeve-like trigger element (82). If appropriate, in order to minimize the surface pressure, the contact surface (24) has a curvature corresponding to the inner wall (59), cf. FIG. 10.

As an alternative to the pressure bars (21), it is also possible to use draw hooks, cf. FIG. 11. These draw hooks (21) are formed integrally in the upper area of the housing. When the spring-energy reservoir (50) is tensioned, they engage around the ram plate (73) of the piston-actuating ram (60) from above. In order to provide sufficient free space for the outwardly pivoting draw hooks (21) upon actuation of the injector, the trigger cap (81) in this variant is configured at least in some areas as a frustoconical jacket.

The fixing area (41) for receiving the insertable cylinder/piston unit (100) is located below the jacket section (31), cf. FIG. 10. The fixing area (41) comprises, for example, eight spring hooks (42) aligned parallel to the centre line (5). The spring hooks (42) each have an at least two-flank rear engagement in order, if appropriate, to receive the cylinder/piston unit (100) without play.

According to FIG. 10, the mutually opposing flanks (43, 44) of the two-flank rear engagement of spring hooks (42) form an angle of 127 degrees with respect to centre line (5), for example. The lower flank (44) has a cone angle of 45 degrees, with its corne tip lying on the centre line 5, as viewed in the direction of the nozzle (106), below the end face (17). The length and the spring rate of the spring hooks (42) are such that the cylinder (101) can be inserted without plastic deformation of the spring hooks (42).

Figure 9:
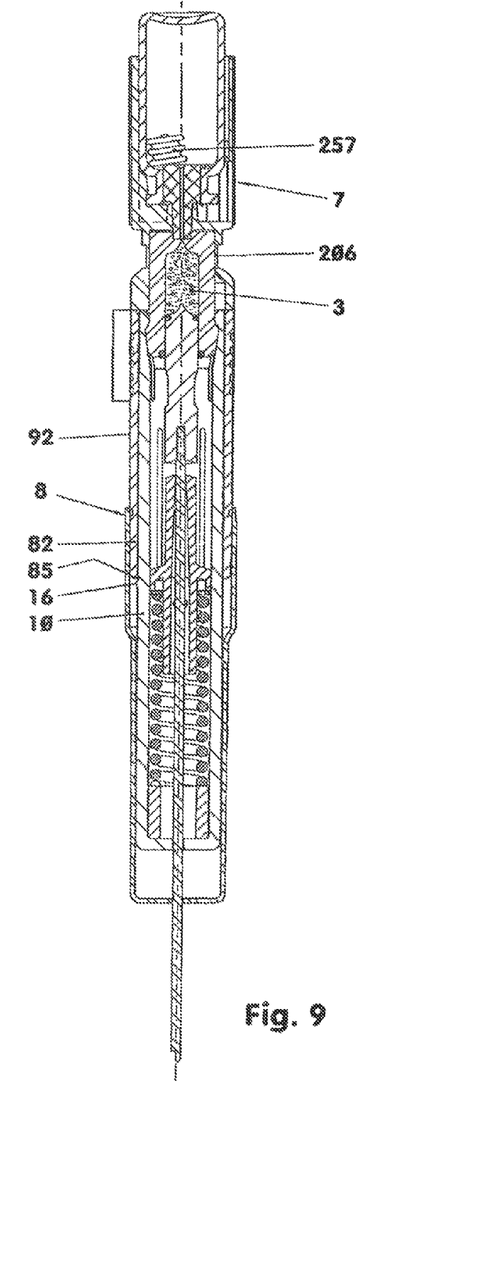
FIG. 9 shows the same as FIG. 8, but with the content of the container pumped back into the cylinder of the cylinder/piston unit.

To be able to securely fix the housing (10) together with the spring element (50) and the piston-actuating ram (60) in the trigger element (82) upon assembly, the housing (10) has, in an area between the cams (22), a lens-shaped elevation (16), cf. FIG. 9, via which the housing (10) bears on the edge (85) of the trigger element (82).

The cylinder (101), cf. FIG. 10, is for example a transparent, thick-walled pot whose outer wall, cylindrical at least in part, bears a for example circumferential locking rib (102) which bears on the flanks (43, 44) of the rear grip of the spring hooks (42) in a dimensionally stable manner. In the area of the rear end face of the cylinder (101), a collar (119) for receiving a sealing element (105) is situated on the upper end of the cylinder inner wall (109). If appropriate, the collar can also be a radial, annular turned-in groove that surrounds parts of the sealing element (105) with a form fit. Alternatively or in addition, the sealing element (105) can be adhesively bonded to the cylinder The sealing element (105) is depicted as an O-ring in the illustrative embodiments. However, it can also be a quad ring, a lip seal or another equivalent sealing element.

Located in the centre of the bore of the cylinder (101), whose cylinder floor matches the contour of the front piston end face at least approximately, there is a short cylindrical, nozzle-like bore (106). Its diameter is ca. 0.1 to 0.5 millimetre. This bore (106) is one to five times as long as its diameter. It ends in a cylindrical or conical recess (107) of the floor-side, outer end face (103) of the cylinder (101). The recess (107) constitutes at least approximately the front one to two millimetres of a Luer tapered bore. This end face (103) can additionally be fitted with an adhesive ring (104) to enhance the safety of use.

The cylinder (101) is, for example, made from the amorphous thermoplastic cycloolefin copolymer (COC). This material is virtually impermeable to water vapour, which permits long-term storage of the injection solution.

The rodless piston (111) sits in the for example cylindrical or conical bore of the cylinder (101). At its at least approximately conically shaped front end face, the piston (111), made of the Teflon® derivative tetrafluoroethylene/hexafluoroethylene copolymer (FEP) for example, has an axial annular groove (112) for receiving a sealing ring (114) or a permanently elastic sealing compound. Teflon® is a U.S. registered trademark of E. I. DuPont De Nemours and Company, Inc., of 1007 Market Street, Wilmington, Del. 19898. The length of the piston (111) is chosen such that the inserted piston (111), cf. FIG. 8 or 11, protrudes at least one millimetre beyond the rear top edge of the cylinder. The middle area of the piston (111) is narrowed. The peripherally narrowed area has a length corresponding to ca. 30% of the total length of the piston. The narrowed area has a diameter that is 16 to 20% smaller than the maximum internal diameter of the cylinder in the area of the cylinder interior (110) receiving the solution. The front transition lying between the narrowed area and the front, i.e. in this case bottom, piston area has a cone angle of 35 to 40 degrees with respect to centre line (5), for example. The other, rear transition has a cone angle of between 35 and 90 degrees with respect to centre line (5).

Figures 12, 13, 14:
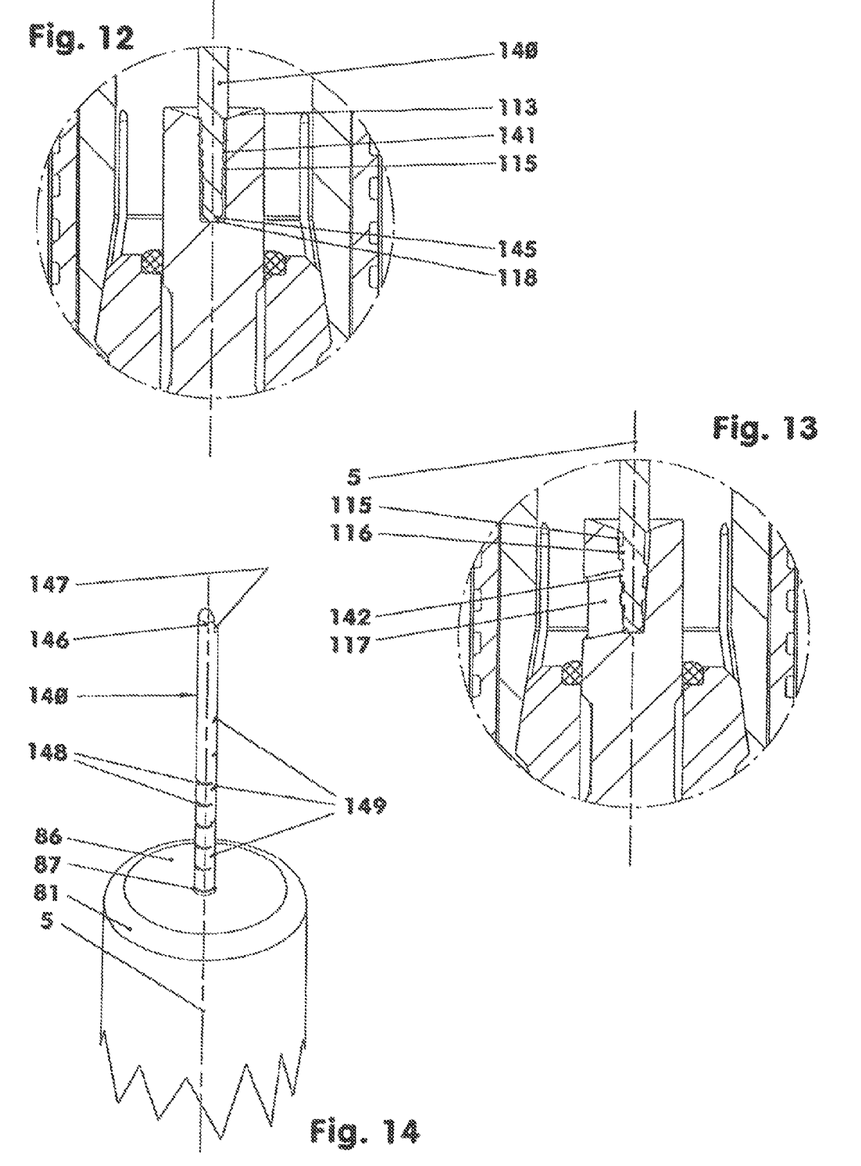
FIG. 12 shows an enlarged detail from FIG. 8.
FIG. 13 shows an alternative enlarged detail from FIG. 8.
FIG. 14 shows a perspective partial view of the housing with pump rod.

In the rear, for example frustoconical, end face (113) of the piston (111), there is a central, conical piston recess (115) with the floor (118), cf. FIG. 12, for coupling the pump rod (140). The cone angle of the piston recess (115) is, for example, one degree. At its lower end, according to FIG. 12 among others, the pump rod (140) has a conical V-thread (141) for coupling to the piston (111). The cone angle of the V-thread (141) is six degrees, for example. When the pump rod (140) is turned into the piston recess (115), the thread pitch of the V-thread (141) presses in the necessary counter-thread. The turning-in operation is completed when the front end of the pump rod (140) contacts the floor (118) with the narrow tip of the frustoconical end face (145).

FIG. 13 shows, as the coupling between the pump rod (140) and the piston (111), a conical trapezoid thread (142) that engages in a piston recess (115) in which at least one partial pitch (116) or a cam is arranged. The partial pitch (116) shown extends in cross section, i.e. perpendicular to the centre line (5), over 30 to 60 degrees. The axial forces to be transmitted from the pump rod (140) to the piston (111) are conveyed only via the partial pitch (116). For reasons of production engineering, an oblong hole (117) is located below the partial pitch.

Both separate threads (141, 142) used for coupling purposes require only minimal screwing-in and screwing-out forces. Other releasable couplings can of course also be used, for example, a key/keyhole system or a simple catch system.

The pump rod (140) has, for example, a constant cross section and a smooth surface along most of its length. Its maximum diameter in the illustrative embodiment is ca. two millimetres. It is made, for example, of a polyamide reinforced with glass fibres. At its rear end, which protrudes from the bore (87) of the trigger cap (81), it has two differently graduated scales (148) and (149), cf. FIG. 14 among others. The scale (148) is for a cylinder/piston unit (100) whose cylinder (101) has an average internal diameter of seven millimetres, while the other scale (149) is for a cylinder (101) with an internal diameter of six millimetres. The different-sized cylinders (101) can be inserted into the injector alternately.

Both scales (148, 149) each have horizontal division marks. These division marks lie in planes that are oriented perpendicular to the centre line (5). Each division mark has, for example, the length of half the circumference of the pump rod. The division marks of one scale (148, 149) all lie above one another. They can, for example, be coloured, black or white division marks or can be formed as notches in the pump rod. Instead of the division marks, dots or numbers can also be used.

If appropriate, the rear end of the pump rod (140) can be provided with a structure, for example transverse or longitudinal grooves, a fluting or the like, in order to improve its grip. The cross section can also be flattened in areas, for weight reduction, or can have a greater diameter than the area that extends through the piston-actuating ram (60).

Figure 16:
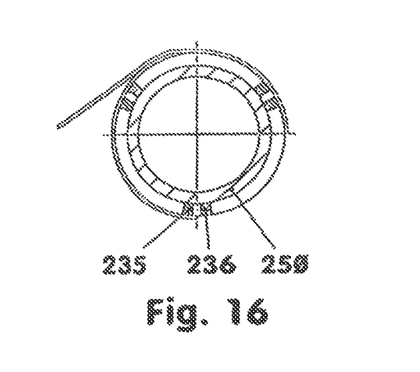
FIG. 16 shows a cross section of FIG. 15.

According to FIG. 16, the front scale (148) assigned to the larger cylinder is lengthened by a half cylinder (146) to make the allocation clear. The two lower division marks located directly on the level of the floor (86) mark the nominal volume of the respective cylinders (101). The in each case upper division mark indicates that the piston (111) is pushed completely into the cylinder (101). Each of the other division marks of the scales (148, 149) represents 0.1 millilitre, for example.

The spring-energy reservoir (50) or drive unit of the disposable injector is arranged between the piston (111) and the floor (39).

The spring-energy reservoir (50) is a helical compression spring, arranged on the piston-actuating ram (60) with the ram plate (73). It is supported on the upper floor (39) of the housing (10) with interpositioning of a spacer sleeve (19). The spring-loaded piston-actuating ram (60) is supported on the pressure bars (21) of the housing (10) by means of the ram plate (73).

Above the ram plate (73) the piston-actuating ram (60) has a guide pin (62). The latter guides the helical compression spring (50) or is guided thereby. Located centrally below the ram plate (73) in the extension of the guide pin (62) is the piston slide (76), which acts on the piston (111) when the disposable injector is actuated. The piston slide (76) has a frustoconical, forwardly curved end face (77), cf. FIG. 10 among others. With this end face (77), it contacts the matchingly shaped end face of the piston (111). Both cones have at least approximately the same cone angle.

In the illustrative embodiment, the piston slide (76) ends 2 to 4 millimetres, for example, above the piston (111). The piston-actuating ram (60) has a through-bore (63) whose upper half is substantially cylindrical, while the lower half narrows conically towards the bottom. In the area of the lower end face (77), the bore is only one to two tenths of a millimetre larger than the external diameter of the piston rod.

FIGS. 6 and 8 to 11 show a pressure bar injector with a trigger unit (80) that almost completely encloses the housing. The trigger element (82), as part of the trigger unit (80), is also a trigger sleeve here. The substantially cylindrical trigger sleeve (82), made of acrylonitrile butadiene styrene, ABS, for example, has as its end face the return flank (84) with the inwardly lying edge (85). A trigger cap (81), which surrounds the rear end of the housing (10), is secured on the trigger element (82). The trigger cap (81) is for this purpose pushed over the rear end of the trigger element (82).

Directly above the return flank (84), the widened area (83) is located in the trigger cap (81). Above the widened area (83), the trigger cap (81) bears slidably on the outer wall (13) of the housing (10).

To secure the trigger cap (81) on the trigger element (82), the trigger element (82) has, for example, an annular groove (56) into which a peripheral web or locking cam (55) of the trigger cap (81) engages. If appropriate, in order to facilitate assembly, part of the trigger cap (81) is provided with longitudinal slits, for example two thereof.

Located in the lower area of the trigger element (82), in the outer wall thereof, are several circumferential channels (57), cf. FIG. 11, or another comparable structure. The channels (57) are, for example, equidistant from one another and extend over 10 to 30 millimetres of the length of the trigger element (82).

The cylindrical trigger element (82) is ensheathed along its entire length by an adhesive label (91). The adhesive label (91) itself is, for example, a paper and/or film strip coated on one side with an adhesive in some areas. The film strip once surrounds, for example in a single layer, the combination of container adapter (200) and trigger element (82). It is composed, as tamper-evident seal (90), of three separate strips that can each be detached from one another via a perforation (96). The upper strip is the main part (92), the middle strip is a tear-off banderole (94) with a two to three centimetre long tear-off tab (95), and the lower strip is the adapter part (93). The main part (92) and the adapter part (93) carry an adhesive layer, with which they are secured on the trigger element (82).

The container adapter (200), centred on the cylinder (101) of the cylinder/piston unit (100), bears on the lower end face (58) of the trigger element (82). The at least in some areas approximately cylindrical outer surface of the container adapter (200) has the same external diameter as the likewise cylindrical outer surface of the trigger element (82) in the vicinity of its end face (58).

The container adapter (200) is a pot-like component which receives, in a container area (221), a displaceably mounted, closed container (250) and a dual adapter (240), for example a Luer lock stopper with through-channel. At the same time it has a sleeve-like adapter area (201) with which it is supported on the housing (10) when centred on the cylinder (101).

The adapter area (201) is a beaker which fits tightly around at least the lower quarter of the cylinder (101) and which ends in an intermediate floor (211) before the end face (103) of the cylinder (101). It has an Upper support zone (202) oriented towards the end face (58), and a window zone (205) which is oriented towards the intermediate floor (211) and which can also be omitted in the case of a transparent adapter area (201) material.

The support zone (202) joined flush to the trigger element (82) has, for example, three or five contact webs (203) which protrude radially inwards, towards the centre line (5), and which extend as far as the outer wall of the cylinder (101). The contact webs (203) touch the end face (17) of the housing (10).

The narrowed window zone (205) bears tightly on the cylindrical outer wall of the cylinder (101). The cylinder (101) has a cylinder floor (108) located at near the bottom of the cylinder interior (110). Two almost rectangular windows (206) lying opposite each other are arranged in said window zone (205). The windows (206) have a width which corresponds to at least the diameter of the piston (111). The window centres are located at the height of the cylinder floor (108), cf. FIG. 6. In the disposable injector position shown there, it is possible, with the aid of the windows (206), to check by transmitted light that the injection solution (3) is free from bubbles.

The for example planar intermediate floor (211) contacts the end face (103) of the cylinder (101) at the adhesive ring (104) thereof protected by a film, and for example via an annular web (214) with a semi-toroid surface. The web (214) encloses a central recess (212) of the intermediate floor (211). The central recess (212), which is lengthened by a support tube (213) to at least three times the thickness of the intermediate floor, has a Luer tapered cone as at least part of its inner wall.

Figure 6:
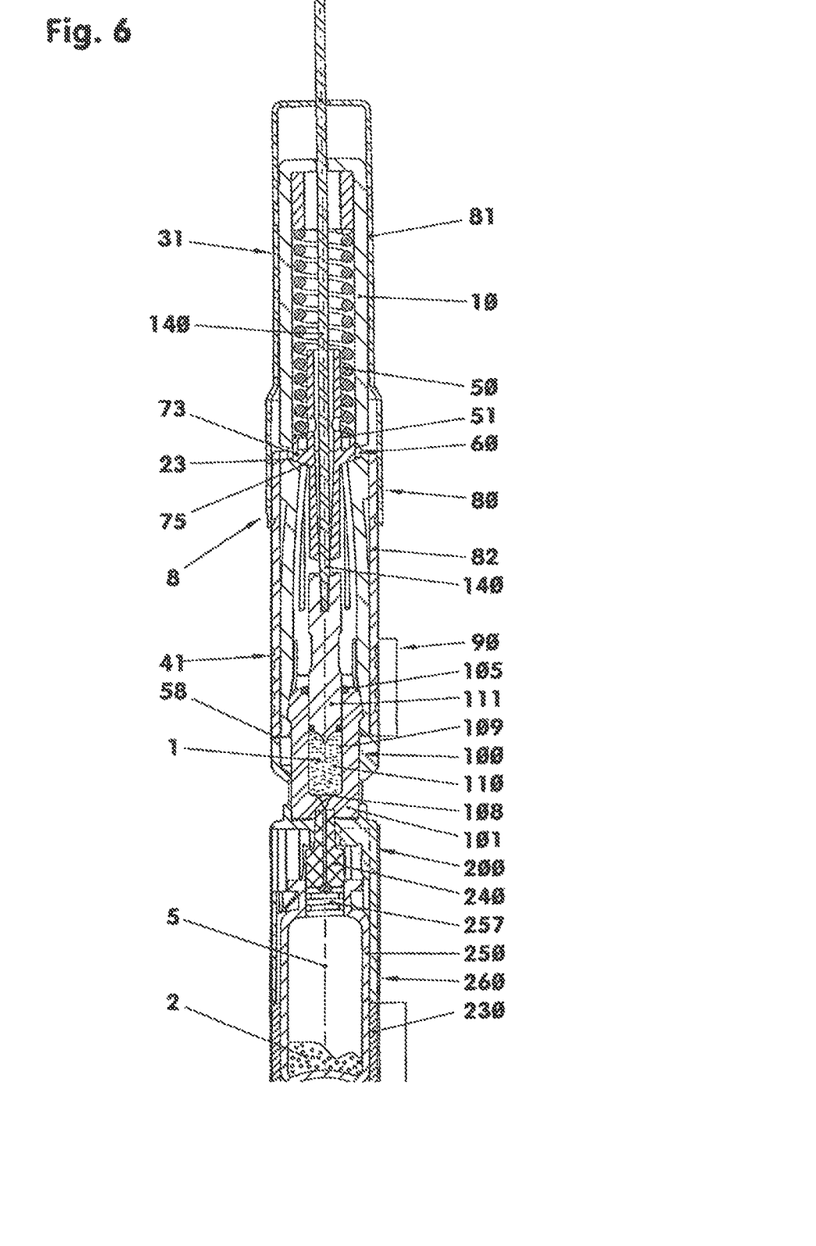
FIG. 6 shows a disposable injector with a solvent-filled cylinder/piston unit, and with an attached container partially filled with active substance.
Figures 7, 7A:
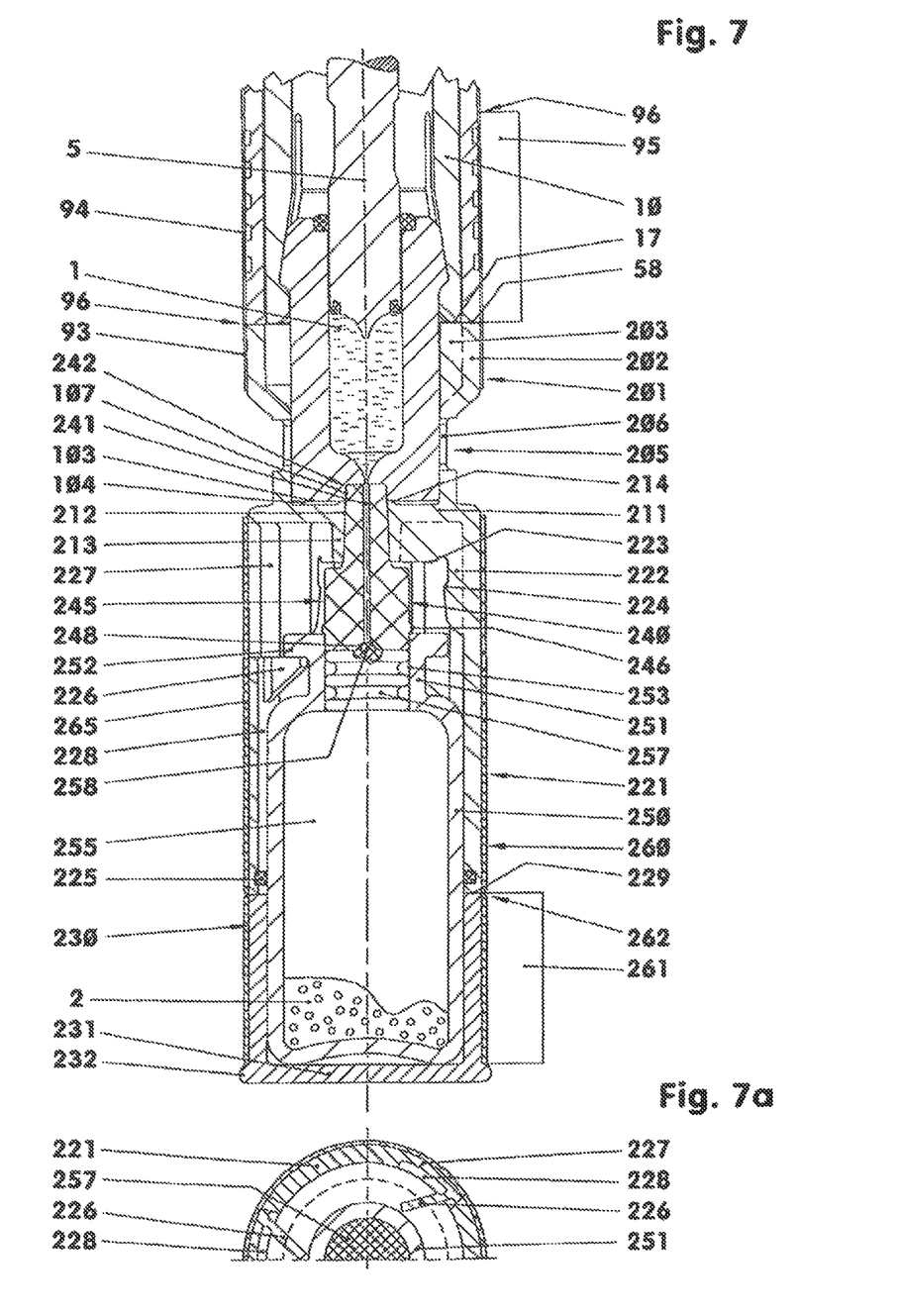
FIG. 7 shows a container adapter of the disposable injector according to FIG. 6.
FIG. 7*a* shows a cross section of FIG. 7 at the level of the container stopper.

In the tubular container area (221) of the container adapter (200), the support tube (213) is surrounded by, for example, three radially arranged locking webs (222) each distributed through 120°. For subsequent fixing of the container (250), the locking webs (222) form, on the one hand, axial abutments (223) and, on the other hand, engage-behind locks (224), cf. FIGS. 7 and 7a. Located between the locking webs (222) there are three slide recesses (227), with a foldable locking hook (226), i.e., abutment, arranged upstream of each of them. The at least approximately triangular foldable locking hooks (226), which engage behind the flange edge (252)

of the container (250) according to FIGS. 6 and 7, are each arranged in a longitudinal groove (228) of the container area (221). According to FIG. 7a, they protrude inwards when folded out, one of their side faces in each case lying in an imaginary plane tangential to the container stopper (257). In the folded-in state, cf. FIG. 8, the foldable locking hooks (226) fit snugly into the longitudinal grooves (228), where they are held by the container (250).

The slide recesses (227) are covered in a sterile manner by a gas-tight, elastic valve tube (265) for example.

The container area (221), of which the internal diameter is only slightly greater than the maximum external diameter of the container (250), extends as far as the lower third of the container (250) according to FIG. 7. There, it ends in a smooth end face (229), for example. If appropriate, an elastic sealing ring (225) is situated in an annular groove above the end face (229) and provides a sterile closure of the join between the container (250) and the inner wall of the container area (221).

The end face (229) is adjoined by a cap (230) which, for example, completely surrounds the rear area of the container (250). The cross section of the cap, measured transverse to the centre line (5), corresponds, except for the annular grooves (228), to the cross section of the container area (221). The cap (230) has a floor (231), which can protrude a few millimetres beyond the radial outer contour of the cap. If appropriate, the cap (230) can also be a lattice body or just a clip.

According to FIG. 7, the cap (230) is connected to the container area via a tear-off banderole (260). The tear-off banderole (260), being a tamper-evident seal, covers at least the lower part of the cylindrical outer wall of the container area (221) and of the cap (230). In the area of the end face (229), the tear-off banderole (260) has a circumferential perforation (262) or notch that serves as a predetermined breaking point. In the area of the cap (230), the tear-off banderole (260) is designed as a tear-off tab (261). When the latter is unwound from the cap (230) counter to the adhesion and the perforation (262) is severed, the cap (230) can be withdrawn from the container. In this process, the foldable locking hooks (226) prevent the container (250) from being pulled out of the container adapter (200).

Alternatively, in order to do without the valve tube (265) and the sealing ring (225), the tear-off banderole (260) can also cover the slide recesses (227). In this case, the tear-off banderole (260) has to close the slide recesses (227) in a gas-tight and sterile manner, cf. FIGS. 6, 8 and 9.

The container (250) is a glass vial, for example, or a lyophilisate vial with a narrowed neck (251) and a flange edge (252). The flange edge (252) protrudes from the neck (251). However, its external diameter is smaller than the maximum external diameter of the container. The transition between the neck (251) and the cylindrical outer wall of the container (250) is rounded with a large radius, which corresponds, for example, to twice the wall thickness of the container.

The opening (253) of the container (250) is closed, for example, by a container stopper (257) made of rubber. On its top face, the container stopper (257) has a central frustoconical sealing knob (258).

A dual adapter (240), made of rubber or of an elastomer for example, is arranged between the container (250) and the intermediate floor (211). According to FIG. 7, the dual adapter (240), which has at least one through-channel (241) extending through it in the longitudinal direction, sits, on the one hand, with its container section (245) partially in the container opening (253) and, on the other hand, with its Luer lock section (242) in the Luer lock tapered cone recess (212) of the intermediate floor (211).

The container section (245) of the dual adapter (240) has a cylindrical shape whose diameter is slightly greater than the internal diameter of the opening (253), in order to obtain a sealed fit. The cylindrical outer contour additionally has a peripheral web (246). According to FIG. 7, the edge of the opening bears on this peripheral web (246) for transport safety. The end face (247) of the dual adapter (240) directed towards the container stopper (257) has at its centre a conical depression (248) into which the through-channel (241) opens and into which the sealing knob (258) of the container stopper (257) protrudes sealingly.

Around the depression (248), the end face (247) has a structure comparable to a Hirth serration, cf. FIG. 8. The structure, which can also be formed as transverse ribs, knobs and the like, is intended to prevent the container stopper (257) from sticking to the dual adapter (240) over a large surface area. Furthermore, the structure also prevents inadvertent closure of the through-channel (241) when the solution (3) is pumped back, cf. FIG. 9. Alternatively, the stopper (257) can also have such a structure. If both parts (240, 257) have a structure, they ought not to be compatible.

Almost the full surface of the tip of the frustoconical Luer lock section (242) engages sealingly with the recess (107) of the cylinder (101). The cylinder interior (110) and the through-channel (241) thus form a hollow space that is closed off in a sterile manner.

To be able to use the disposable injector, the active substance (2), e.g. the lyophilisate, stored in the container (250) has to be dissolved' in the liquid (1), e.g. water for injection purposes or physiological saline solution, present in the cylinder (101) of the cylinder/piston unit (100). For this purpose, the liquid (1) is to be pumped into the container (250).

In a first step, the tear-off tab (261) is removed from the cap (230), thus severing the perforation (262), and the cap (230) is pulled off from the rear part of the container (250).

In a second step, the container (250) is pushed into the container adapter (200). The container (250) slides forwards along the inner wall of the container adapter (200) until it bears with the flange edge (252) on the abutments (223). At the same time, the engage-behind locks (224) engage round the rear face of the flange edge (252) and thus secure the forward position of the container (250). During the forward movement, the container (250) has forced the foldable locking hooks (226) aside, cf. FIG. 8, and the opening (253) of the container (250) has pushed itself over the peripheral web (246) and sealingly onto the container section (245) of the dual adapter (240). In this process, the container stopper (257) has been pushed inwards out of the opening (253), such that the cylinder interior (110) and the container interior (255) now communicate via the through-channel (241).

The overpressure that arises in the container area (221) as the container (250) is pushed in escapes via the partially lifting valve tube (265).

In a third step, the piston (111) is pushed into the cylinder (101) by means of the pump rod (140) and thus conveys the liquid (1) into the container interior (255), which is now at a slight overpressure, cf. FIG. 8. For this purpose, the pump rod (140) is generally held between the index finger and thumb of the hand operating it.

The lyophilisate (2) dissolves in the liquid (1). The dissolution process can be monitored visually, since the container (250) protruding from the container adapter (200) is transparent., In a fourth step, cf. FIG. 9, the newly resulting solution (3) is pumped back into the cylinder interior (110). For this purpose, the injector is held such that the opening (253) of the container (250) points in the direction of gravity. The piston (111) is pulled into a rear position via the pump rod (140). Through the windows (206), it is possible to check that this has been done free of bubbles.

In a fifth step, the disposable injector is primed by means of the tear-off banderole (94) being separated, with the aid of the tear-off tab (95), from the main part (92) and from the adapter part (93). The channels (57) of the trigger element (82) become visible. The container adapter (200) is now pulled down and removed from the cylinder (101), cf. FIG. 10.

In a final step, the injector is placed on the injection site, and the sleeve-like trigger element (82) is pushed downwards in the direction of the injection site. The pressure bars (21) bend elastically outwards into their actual starting position. In this process, the cams (22) slide out over the edge (85) into the widened area (83). The pressure bars (21), now no longer deformed, free the piston-actuating ram (60), such that the piston (111), under the effect of the spring element (50), moves abruptly downwards in order to empty the cylinder (101), cf. FIG. 11. During the forward movement of the piston (111), the piston friction decreases for a time, since the rear sealing element (105) does not bear with a braking action during passage of the narrowed piston area.

FIGS. 15 to 18 show an alternative container adapter (200). In contrast to the container adapter (200) according to FIG. 7, it has a secured cap (230) and three-part banderole (260).

The container area (221) has, for example, two or more, according to FIGS. 15 to 18 in each case three, quadruple locking recesses (216) which extend from the end face (229) in the direction of the adapter area (201). The quadruple recesses (216) each have two mutually opposite front locking notches (217) and two rear locking notches (218). According to FIG. 15, two locking hooks (235, 236), with their backs facing each other, engage in the front locking notches (217). Between the pair of locking hooks (235, 236), there is a free space that allows the locking hooks (235, 236) to be pushed into the quadruple recess (216).

Figure 15:
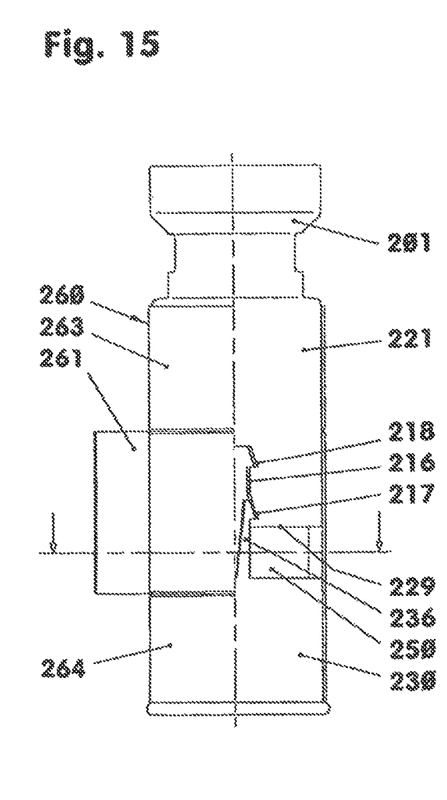
FIG. 15 shows an external view of a container adapter with a fixed cap and partially cut away banderole.

According to FIG. 15, the container (250) is in the position that is also shown in FIG. 7. The locking hooks (235, 236) and the free spaces between the locking hooks are covered by means of the tear-off banderole (260). The tear-off banderole (260) avoids the parts (221) and (230) being pushed together.

Figure 17:
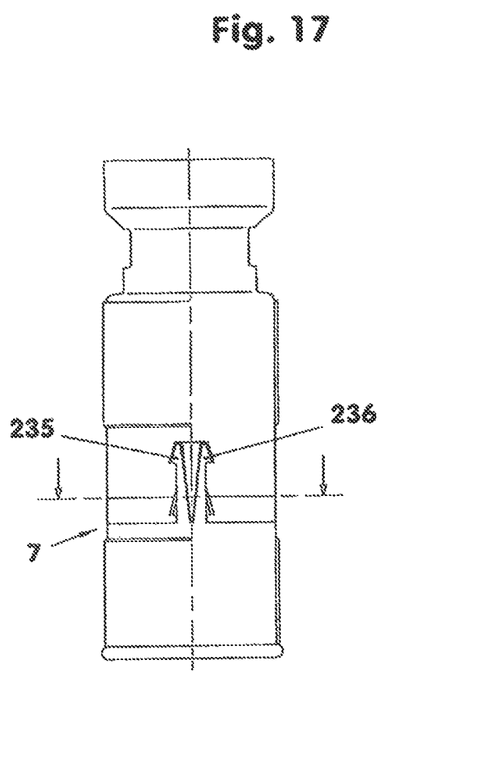
Figure 18:
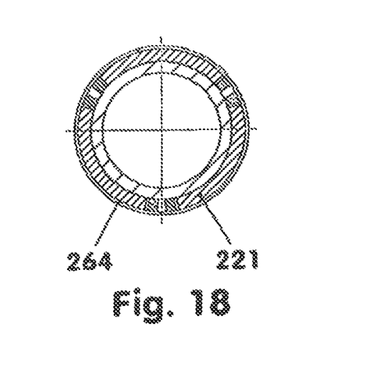
FIG. 18 shows a cross section of FIG. 17.

In FIG. 17, the container adapter (200) is shown in the state when pushed together. To permit the pushing together, the tear-off tab (261) was first completely unwound from the container adapter (200). The container (250) together with the cap (230) was then displaced in such a way that the locking hooks (235, 236) are engaged in the rear locking notches (218). The container (250) has then reached the position also shown in FIG. 8. By means of the locking engagement, the container (250) is enclosed completely in the container adapter (200).

The container adapter (200) is here made of a transparent material, such that the dissolving of the lyophilisate can be observed.

If appropriate, a very large number of locking hooks are used instead of a few, such that when the cap (230) is mounted on the container area (221) a mutual locking engagement is possible without the need for an exact positioning of the parts (230, 221) relative to each other. It is also conceivable for all or some of the locking hooks to be arranged on the container area (221), while the corresponding locking recesses are formed in the cap.

Instead of the locking hooks (235, 236) and the locking recesses (216), a longitudinally slotted support ring can also be arranged between the container area (221) and the cap (230) and is supported via the tear-off banderoles. Here, the container (250) can be pushed into the container area (221) after removal of the support ring.

In these two variants, the container (250), if appropriate, sits in the cap (230) by way of a clamp fit or adhesive bond.

In the case of injectors in which the piston-actuating ram (60) is guided rectilinearly with slight play in at least part of the housing (10) and the piston-actuating ram (60) has adequate bending strength, it is possible for just one pressure bar (21) to be used instead of two or more pressure bars (21).

In the variants shown in the figures, the individual contact zone between the pressure bar (21) and the ram plate (73) is designed as surfaces (23) and (75), which are able to slide on each other upon contact. In a particular embodiment, each surface (23) of the individual pressure bars (21) can support a roller which, when the injector is actuated, rolls away as a roller bearing, therefore with low friction, on the surface (75) of the ram plate.

Except for the spring elements (50, 52), an optional piston plate and, for example, the bearing rollers of the support bars (21), all the parts of the above-described disposable injectors are made of plastics or of plastic-like or rubber-like materials.

List of Reference Symbols:
1 water for infusion purposes, solvent
2 lyophilisate, active substance
3 injection solution
5 centre line of injector, longitudinal direction
6 direction of triggering movement of (82), downward movement, directional arrow
7 transfer-pumping position
8 locked position
9 release position, trigger position
10 housing, one-piece
13 outer surface, cylindrical
16 elevation, lens-shaped
17 end face, front, bottom
19 spacer sleeve
21 pressure bars, support bars; draw hooks
22 cams
23 support surface
24 contact surface
25 engage-behind flank
26 flexural beam
31 jacket area
33 apertures
38 bore
39 floor
41 fixing area for the cylinder/piston unit
42 spring hooks
43 flank, upper
44 flank, lower
50 spring element, helical compression spring, spring-energy reservoir
51 washer, planar
52 spring elements on (21)
55 locking cams
56 annular groove of (82)
57 channels of (82)
58 end face of (82)
59 inner wall of (82)
60 piston-actuating ram
62 guide pin
63 bore, through-bore
73 ram plate
75 collar surface, conical
76 piston slide
77 end face of piston slide, conical 80 trigger unit
81 trigger cap
82 trigger element
83 widened area
84 return flank
85 edge, sharp
86 cap floor
87 bore
90 tamper-evident seal, banderole, safety element
91 adhesive label
92 main part of (91)
93 adapter part of (91)
94 tear-off banderole
95 tear-off tab
96 perforations, predetermined breaking points
100 cylinder/piston unit
101 cylinder
102 locking rib
103 end face
104 adhesive ring
105 sealing element
106 bore, nozzle
107 recess in the end face
108 cylinder floor
109 cylinder inner wall
110 cylinder interior
111 piston
112 annular groove
113 end face, rear; cone
114 sealing ring, seal, sealing element
115 piston recess, bore
116 partial pitch, cam
117 oblong hole
118 recess edge of (115)
119 collar on (101)
140 pump rod
141 tapered thread, V-thread
142 special thread, tapered thread
145 end face, frustoconical
146 half cylinder
147 shoulder (for small cylinder)
148 markings, half notches for large cylinders
149 markings, half notches for small cylinders
200 container adapter
201 adapter area
202 support zone
203 contact webs
205 window zone, narrowed
206 window, on both sides
211 intermediate floor
212 recess, central
213 fixture, support tube
214 web, annular, semi-toroid
216 quadruple locking recess
217 locking notches, front
218 locking notches, rear
221 container area
222 locking webs
223 abutments
224 engage-behind locks
225 sealing ring
226 foldable locking hooks, abutments
227 slide recesses
228 longitudinal grooves
229 end face
230 cap
231 floor
232 edge
235 locking hook, left
236 locking hook, right
240 dual adapter, elastic
241 through-channel
242 Luer lock section
245 container section
246 peripheral web
247 end face
248 depression
249 Hirth serration
250 container, ampoule
251 neck
252 flange edge
253 opening
255 container interior
257 container stopper, stopper, elastic
258 sealing knob, elastic
260 tear-off banderole
261 tear-off tab
262 perforations, predetermined breaking points
263 edge part, rear
264 edge part, front
265 valve tube, elastic

What is claimed is:

1. A method for preparing a solution (3) from a solvent (1) and an active substance (2) in and on a disposable injector including a housing (10) housing an injector-side cylinder/piston unit (100) including a cylinder (101) in operable arrangement with a piston (111), the cylinder (101) having an interior (110) including a cylinder floor (108) proximate a nozzle (106) for injecting the prepared solution (3) into a patient, the method comprising the steps of:

before the solution (3) is prepared, the solvent (1) is stored in the injector-side cylinder/piston unit (100), while the active substance (2) is contained in an interior (255) of a container (250) which is mounted upstream of the cylinder/ piston unit (100) below the injector-side cylinder piston unit (100) and which is closed by a stopper (257), a dual adapter (240) with a bore extending through it is arranged between the cylinder/piston unit (100) and the stopper (257), the bore of the dual adapter (240) in direct contacting and fluid flow relationship with the nozzle (106) of the cylinder (101) before the solution (3) is prepared, to establish a connection between the interior (110) of the cylinder (101) and the interior (255) of the container (250), the container (250) is displaced towards the dual adapter (240) and forces the stopper (257) out, the solvent (1) flows into the interior (255) of the container (250), by the direct pushing in of the piston (111), and the active substance (2) dissolves there in the solvent (1) to form a solution (3), and the solution (3) is pumped into the cylinder/ piston unit (100) by direct pulling back of the piston (111).

2. The method according to claim 1, wherein the solution (3) is a suspension or an emulsion.

* * * * *